US00PP20846P2

(12) United States Plant Patent
Yates

(10) Patent No.: US PP20,846 P2
(45) Date of Patent: Mar. 16, 2010

(54) *BEGONIA* PLANT NAMED 'YASPMON'

(50) Latin Name: *Begonia hybrid*
Varietal Denomination: Yaspmon

(76) Inventor: Frederic C. Yates, Holmes Chapel Rd. Cheshire, Congleton CW12 4SP (GB)

( * ) Notice: Subject to any disclaimer, the term of this patent is extended or adjusted under 35 U.S.C. 154(b) by 0 days.

(21) Appl. No.: 12/317,767

(22) Filed: Dec. 29, 2008

(51) Int. Cl.
*A01H 5/00* (2006.01)

(52) U.S. Cl. ..... Plt./343

(58) Field of Classification Search ..... Plt./343
See application file for complete search history.

*Primary Examiner*—Annette H Para
(74) *Attorney, Agent, or Firm*—Penny J. Aguirre

(57) ABSTRACT

A new cultivar of hybrid *Begonia*, 'Yaspmon', characterized by large, single, pink-orange colored flowers, its compact, mounded to semi-trailing plant habit and its suitability for use in baskets, patio containers, and as a garden bedding plant.

2 Drawing Sheets

RELATED APPLICATIONS

This application is co-pending with U.S. Plant patent applications for cultivars derived from the same breeding program entitled *Begonia* Plant Named 'Yamance' (U.S. Plant Pat. No. 19,817), *Begonia* Plant Named 'Yagance' (U.S. Plant Pat. No. 19,777), and *Begonia* Plant Named 'YABOS' (U.S. Plant Pat. No. 20,093).

Botanical classification: *Begonia* hybrid.

Cultivar designation: 'Yaspmon'.

BACKGROUND OF THE INVENTION

The present invention relates to a new and distinct cultivar of *Begonia* plant of hybrid origin, botanically known as *Begonia* 'Yaspmon' and will be referred to hereafter by its cultivar name, 'Yaspmon'.

The new cultivar was derived from a controlled breeding program conducted by the inventor at his nursery in Congleton, Cheshire, U. K. The overall purpose of the breeding program is to make selections of *Begonia* plants with compact plant habits suitable for gardens, baskets and patio containers. 'Yaspmon' was selected as a single unique plant in 2005 and derived from a cross made between an unnamed proprietary plant of hybrid *Begonia* as the female parent plant and *Begonia boliviensis* 'YABOS' (U.S. Plant Pat. No. 20,093) as the male parent.

Asexual reproduction of the new cultivar was first accomplished by terminal stem cuttings in Congleton, Cheshire, U. K. in 2005 by the Inventor. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Yaspmon' as a new and distinct cultivar of *Begonia*.

1. 'Yaspmon' exhibits large single flowers that are pink-orange in color.
2. 'Yaspmon' exhibits a compact, semi-trialing habit.
3. 'Yaspmon' is suitable for use in baskets, patio containers, and garden bedding.

In comparison, the unnamed female parent of 'Yaspmon' differs from 'Yaspmon' in having double flowers and the male parent, 'YABOS', differs from 'Yaspmon' in having smaller flowers that are red-orange (less pink) in color. Its sibling selection, 'Yamance', differs from 'Yaspmon' in having a more trailing plant habit and smaller male flowers while its sibling selection, 'Yagance', differs in having a more trailing plant habit and bi-colored flowers. 'Yaspmon' can also be compared to 'Bonfire' (U.S. Plant Pat. No. 15,108), which differs from 'Yaspmon' in having flowers that are red-orange rather than pink-orange in color.

BRIEF DESCRIPTION OF THE DRAWING

The accompanying colored photographs illustrate the overall appearance and distinct characteristics of the new *Begonia*. The photographs were taken in September of a plant approximately 6 months in age as grown in a two-liter container in Swavesey, Campbridgeshire, U.K.

The photograph in FIG. 1 provides a side view of 'Yaspmon' in bloom.

Figure 1:
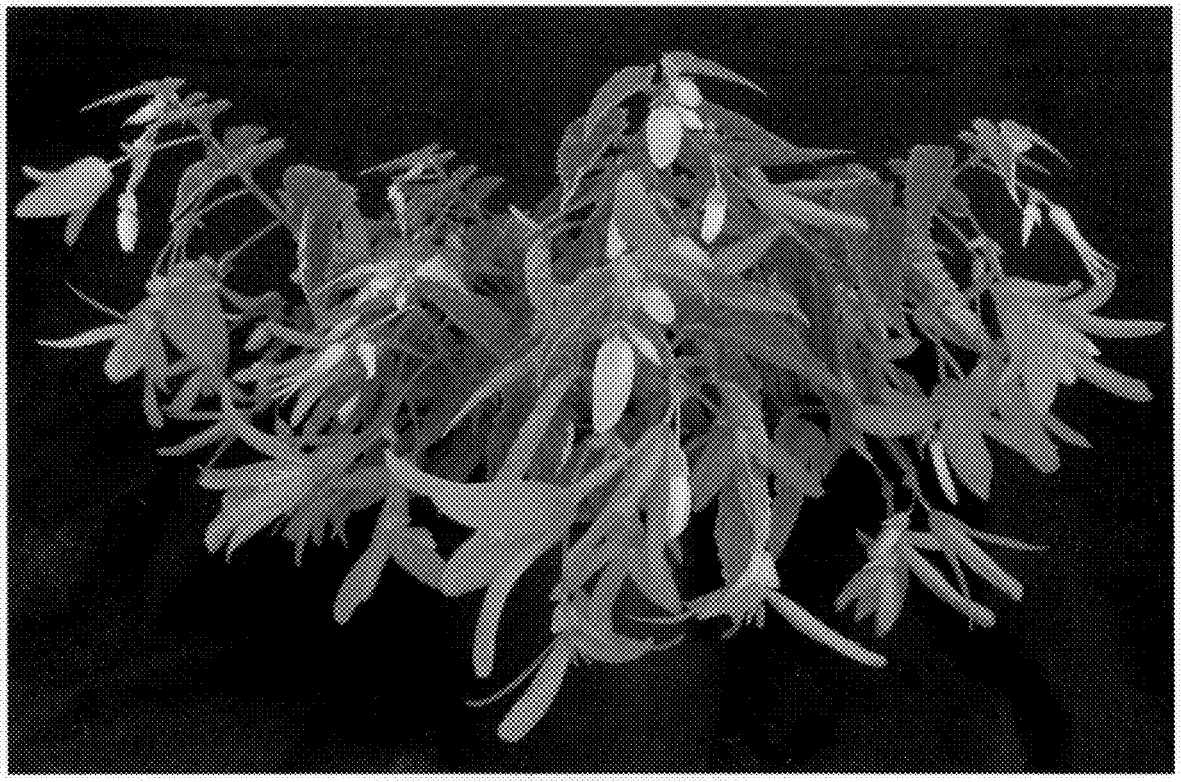
Figure 2:
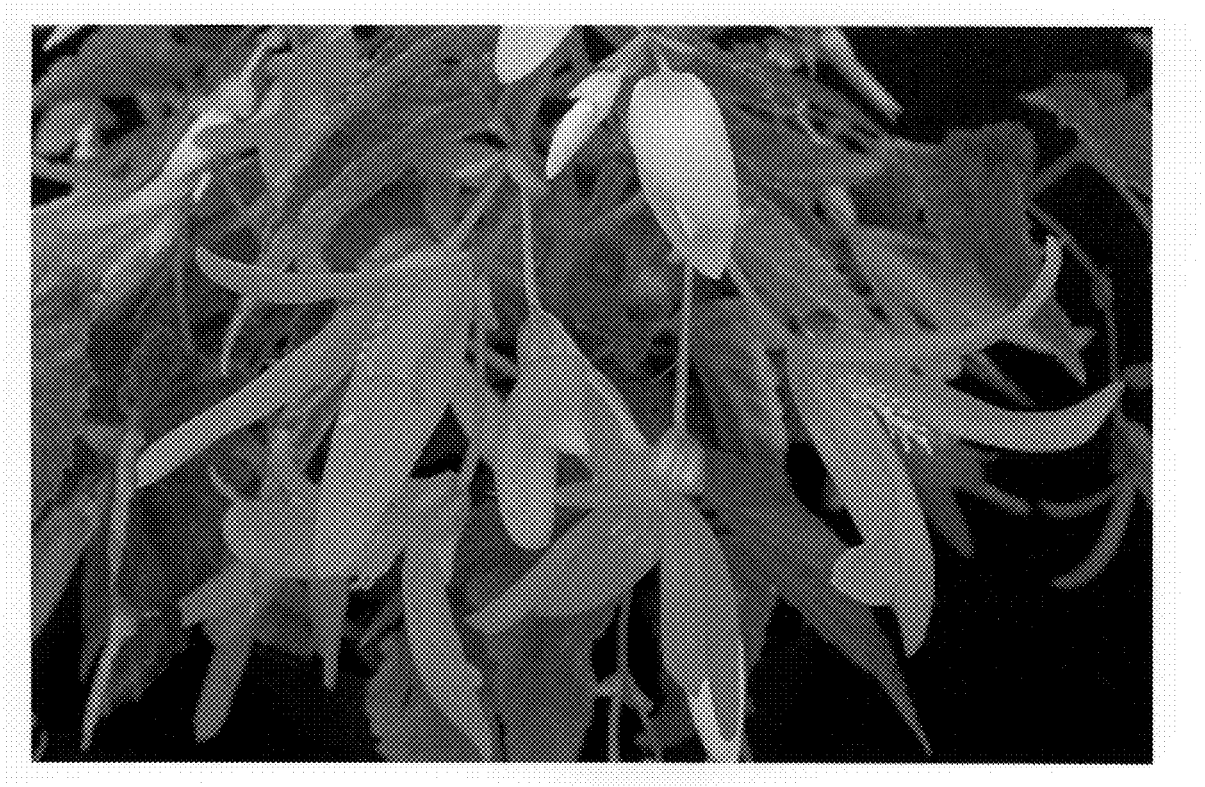

The photograph in FIG. 2 provides a close-up view of the flowers of 'Yaspmon'.

The colors in the photograph may differ slightly from the color values cited in the detailed botanical description, which accurately describe the colors of the new *Begonia*.

DETAILED BOTANICAL DESCRIPTION OF THE PLANT

The following is a detailed description of plants of the new cultivar approximately 6 months in age as grown in two-liter containers under greenhouse conditions with ambient light in Congleton, Cheshire, U. K. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General plant characteristics:

*Plant type.*—Deciduous tuberous perennial, grown for use in baskets, patio containers and as a garden bedding plant.

*Plant habit.*—Compact, mounded to semi-trailing.

*Flowering period.*—From April to November in the U.K.

*Height and spread.*—Reaches about 22 cm in height and about 45 cm in spread.

*Cold hardiness.*—U.S.D.A. Zone 10.

*Culture.*—Grows in any commercial soil or growing media, 12 hours of light is needed for production in the winter months.

*Diseases and pests.*—No susceptibility or resistance to diseases or pests has been observed.

*Root description.*—Fleshy to fibrous with tubers produced for over-wintering.

*Tubers.*—Unevenly globose in shape with upper surface often flattened or slightly depressed in the center, average of 80 mm in diameter (larger on older plants), surface is somewhat lobed and slightly corky, color between 199C and 199D.

Growth and propagation:

*Growth rate.*—Moderately vigorous.

*Propagation.*—Terminal stem cuttings.

*Time required for root development.*—10 to 14 days at 22° C.

*Time required for root development.*—5 to 8 weeks to reach commercial size.

Stem description:

*Stem size.*—Average of 24 cm in length and 1 cm in width with lateral branches about 5 mm in width.

*Stem shape.*—Round, solid.

*Stem color.*—199B when shaded becoming 178A in full sun.

*Stem surface.*—Smooth with young stem weakly pubescent, lenticels absent.

*Internode length.*—Average of 2 cm.

*Branching habit.*—Freely branched on non-flowering nodes.

*Branching angle at emergence.*—About 45°.

Foliage description:

*Leaf shape.*—Lanceolate, asymmetric with one side wider than the other.

*Leaf division.*—Simple.

*Leaf base.*—Rounded on narrower side, cordate on wider side.

*Leaf apex.*—Acuminate.

*Leaf venation.*—Pinnate, color upper surface; closest to 146B, color lower surface; closest to 195A.

*Leaf margins.*—Serrate with short bristles emerging from tips of the teeth.

*Leaf attachment.*—Petiolate.

*Leaf arrangement.*—Alternate.

*Leaf surface.*—Upper and lower surface; sparse fine pubescence.

*Leaf color.*—Upper surface; closest to 147A, lower surface; 147C near veins and tinged with 175B between veins.

*Leaf size.*—Average of 11 cm in length and 3.7 cm in width.

*Leaf fragrance.*—None.

*Petioles.*—About 1.8 cm in length and 2 mm in width, surface is moderately pubescent with simple hairs, color 177B.

*Stipules.*—Triangular in shape, 39B in color and rapidly becoming dry and papery, about 6 mm in length and 3 mm in width.

Flower description:

*Inflorescence type.*—2 to 3 flowered cyme produced sequentially in the axils of the upper leaves, monoecious with terminal male flowers developing before the lateral female flowers.

*Flower persistence.*—Self-cleaning.

*Flower type.*—Single, funnel formed with un-fused tepals.

*Flower fragrance.*—None.

*Peduncles.*—About 4.5 cm in length and 2 mm in width, 42B in color, surface is glabrous.

*Bracts.*—2, present at base of cyme, round in shape, shallowly bifid apex, about 9 mm in length and width, 180B in color, margin is finely serrated.

Male flowers:

*Pedicels.*—About 2.7 cm in length and 2 mm in width, 40A in color, surface is glabrous.

*Flower buds.*—Flattened ovoid in shape, about 3.3 cm in length and 1.5 cm in width, 43C in color.

*Flower size*—About 5.3 cm in length and 6.3 cm in width.

*Flower form.*—Flared un-fused tepals.

*Flower aspect.*—Hanging.

*Outer tepals.*—2, ovate in shape, obtuse apex, rounded base, average of 5.5 cm in length and 2.2 mm in width, glabrous and smooth surface, entire margin, outer surface is 43C in color, inner surface is 43B in color.

*Inner tepals.*—2, linear in shape recurving slightly towards apex, obtuse apex, narrow cuneate base, average of 5.8 cm in length and 1.2 mm in width, glabrous and smooth surface, entire margin, outer surface is a color between 43B and 43C, inner surface is 43B in color.

*Stamens.*—Numerous, connate and forming a tube, about 1.9 cm in length and 1.5 mm in width, 15B in color.

*Filaments.*—About 3 mm in length and 0.5 mm in width, 15A in color.

*Anthers.*—Broadly elliptic in shape, about 1 mm in length and <1 mm in width, 21B in color.

*Pollen.*—Abundant, 8C in color.

Female flowers:

*Pedicels.*—About 3.0 cm in length and 1.5 mm in width, 41B in color, glabrous surface.

*Flower buds.*—Ovoid and weakly flattened in shape, about 1.8 cm in length and 9 mm in width, closest to 43D in color.

*Flower form.*—Flared un-fused tepals.

*Flower aspect.*—Hanging.

*Flower size.*—About 3.3 cm in length and 4.3 cm in width.

*Outer tepals.*—2, ovate in shape, acute apex, rounded base, average of 3.4 cm in length and 1.3 mm in width, glabrous and smooth surface, entire margin, outer surface and inner surface is 43B in color.

*Inner tepals.*—3, linear-elliptic in shape recurving slightly towards apex, obtuse apex, narrow cuneate base, average of 3.7 cm in length and 1 cm in width, glabrous and smooth surface, entire margin, outer surface and inner surface is 43B in color.

*Styles.*—3, cylindrical, connate for basal 1 mm, about 5 mm in length and 1 mm in width, 33B in color.

*Stigmas.*—Bifid in shape and twined around extensions of style, lobes about 8 mm in length and 1 mm in width, 17C in color.

*Ovaries.*—Inferior, triangular in cross section with unequal wings, about 9 mm in length and width (excluding wings), color is 171A merging to 44D at apex of wings.

*Seed.*—Very numerous, ovate-elliptic in shape, to small to measure, N167B in color.

It is claimed:

1. A new and distinct cultivar of *Begonia* plant named 'Yaspmon' as herein illustrated and described.

* * * * *